US009518255B2

(12) United States Patent
Singh et al.

(10) Patent No.: US 9,518,255 B2
(45) Date of Patent: Dec. 13, 2016

(54) MUTANTS OF STAPHYLOKINASE CARRYING AMINO AND CARBOXY-TERMINAL EXTENSIONS FOR POLYETHYLENE GLYCOL CONJUGATION

(71) Applicant: COUNCIL OF SCIENTIFIC & INDUSTRIAL RESEARCH, New Delhi (IN)

(72) Inventors: Satish Singh, Chandigarh (IN); Kanak Lata Dikshit, Chandigarh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/206,984

(22) Filed: Mar. 12, 2014

(65) Prior Publication Data

US 2015/0118212 A1    Apr. 30, 2015

Related U.S. Application Data

(63) Continuation of application No. 12/631,617, filed on Dec. 4, 2009, now abandoned.

(30) Foreign Application Priority Data

Dec. 5, 2008 (IN) ............................ 2757/DEL/2008

(51) Int. Cl.
*A61K 38/00* (2006.01)
*C12N 9/52* (2006.01)
*A61K 47/48* (2006.01)
*C12N 9/48* (2006.01)
*A61K 38/48* (2006.01)

(52) U.S. Cl.
CPC ............. *C12N 9/52* (2013.01); *A61K 38/4886* (2013.01); *A61K 47/48215* (2013.01); *C12N 9/48* (2013.01); *A61K 38/00* (2013.01); *C12Y 304/24029* (2013.01)

(58) Field of Classification Search
CPC .................................................... C07K 14/395
See application file for complete search history.

(56) References Cited

U.S. PATENT DOCUMENTS

2006/0286066 A1*  12/2006  Basran ............ A61K 47/48215
                                                      424/85.1

FOREIGN PATENT DOCUMENTS

WO       WO9903887     *  1/1999    ........... C07K 14/475
WO       WO2009122442  * 10/2009

OTHER PUBLICATIONS

Sako et al, Nucleotide sequence of the staphylokinase gene from *Staphylococcus aureus*. Nucleic Acids Res. (1983a) Nov. 25;11(22):7679-93.*

* cited by examiner

*Primary Examiner* — Sheridan Swope
(74) *Attorney, Agent, or Firm* — Roberts Mlotkowski Safran Cole & Calderon P.C.

(57) ABSTRACT

The present invention relates to the development of new derivatives of a bacterial plasminogen activator, Staphylokinase (SAK), having one or more amino acid residues with single or multiple cysteines at the amino and/or carboxy terminal ends and their conjugation with PEG (Polyethylene Glycol), resulting in new Staphylokinase derivatives that display altered oligomeric states, enhanced thermal and protease stability and extended plasma half-life. Also included is the cloning and expression in a suitable bacterial host; purification of Staphylokinase derivatives to homogeneity and their chemical modification by integrating a PEG molecule to create new biologically active Staphylokinases having higher protein stability and improved in vivo plasma half life, that may enhance the clinical potential of Staphylokinase in thrombolytic therapy for the treatment of cardiovascular diseases.

8 Claims, 6 Drawing Sheets

Map of recombinant plasmid carrying sak gene encoding recombinant SAK

Plasminogen activator activity of representative PEG-conjugated forms of SAK derivatives Trypsin digestion profile of Wild type SAK at different time points Trypsin digestion profile of SAK derivative, SAK 1CCT PEG 20kDa at different time points Trypsin digestion profile of SAK derivative, SAK 2CCT PEG 20kDa at different time points

US 9,518,255 B2

MUTANTS OF STAPHYLOKINASE CARRYING AMINO AND CARBOXY-TERMINAL EXTENSIONS FOR POLYETHYLENE GLYCOL CONJUGATION

CROSS-REFERENCE TO RELATED APPLICATIONS

This application is a continuation of U.S. patent application Ser. No. 12/631,617 which was filed on Dec. 4, 2009 and entitled, "Mutants of Staphylokinase Carrying Amino and Carboxy-Terminal Extensions for Polyethylene Glycol Conjugation", which itself claims benefit of India Application No. 2757/DEL/2008, filed Dec. 5, 2008. The complete disclosure of each of the foregoing applications is hereby fully incorporated herein by reference.

REFERENCE TO SEQUENCE LISTING, TABLE OR COMPUTER PROGRAM

A Sequence Listing is being submitted electronically via EFS in the form of a text file, created Dec. 4, 2009 and named "SAK8001seqlist.txt" (9000 bytes), the contents of which are incorporated herein by reference in their entirety.

TECHNICAL FIELD

The present invention relates to cysteine variants of Staphylokinase (SAK) wherein its amino and carboxy terminal ends are extended by adding extra amino acids having at least one cysteine residue where Polyethylene Glycol (PEG) can be conjugated.

This invention relates to the field of cardiovascular therapeutics, particularly to the thrombolytic drugs that are utilized for the treatment of various cardiovascular diseases.

These fibrinolytic agents, e.g., Tissue plasminogen activator (tPA), Urokinase (UK), Streptokinase (SK), are routinely utilized for the treatment of various circulatory disorders, e.g., deep vein thrombosis, myocardial infarction etc. [Castellino, F. J. (1981) Recent advances in the chemistry of the fibrinolytic system. Chem. Rev. 81; 431-446; Vorcheimer, D. A. (1999) Current state of thrombolytic therapy. Curr. Cardiol Rep. 1; 212-220] due to their ability to activate blood zymogen, plasminogen (PG) into plasmin (Pm) that degrades fibrin mesh of the blood clot into a soluble product, thus, clearing the blockage and leading to coronary recanalization within the body.

The present invention relates to the development of new variants of a bacterial plasminogen activator, Staphylokinase, that has the ability to activate human plasminogen into active plasmin [Lack, C. H. (1948) Staphylokinase: an activator of plasma protease. Nature 161; Lijnen, H. R., Collen, D. (1996) Staphylokinase, a fibrin-specific bacterial plasminogen activator. Fibrinolysis, 10; 119-126; Matsuo, O., Okada, K., Fukao, H., Tomioka, Y., Ueshima, S., Watanuki, M., Sakai, M (1990) Thrombolytic properties of Staphylokinase. Blood 76; 925-929] similar to widely utilized thrombolytic agent, Streptokinase but unlike SK, SAK exerts its plasminogen activation activity in a fibrin specific manner due to its unique ability to display plasminogen activator activity around thrombi as during blood circulation SAK:PG complex is disrupted by the activity of alpha-2 antiplasmin [Lijnen H. R., Van Hoef B., De Cock F., Okada K., Ueshima S., Matsuo O., Collen D. (1991) On the mechanism of fibrin-specific plasminogen activation by staphylokinase. J. Biol. Chem. 266; 11826-11832; Collen, D. (1996) Fibrin-selective thrombolytic therapy for acute myocardial infarction. Circulation 93; 857-865); Collen, D. (1998) Staphylokinase: a potent, uniquely fibrin-selective thrombolytic agent. Nat. Med. 4; 279-284] whereas in a clot environment, binding of SAK: plasmin complex on the fibrin surface become stronger [Sakharov, D. V., Lijnen, H. R. and Rijken, D. C. (1996) Interaction between plasmin (ogen) and fibrin. J. Biol. Chem. 271; 27912-27918]. However, being a bacterial product, clinical administration of SAK creates an allergic reaction and due to its short plasma half-life (3 min) relatively large therapeutic dose may be required. The invention disclosed herein pertains to the development of SAK variants that display higher temperature stability, low protease sensitivity and extended in vivo plasma half-life.

Thus, the present invention relates to the integration of one or more amino acid residues at the amino- and/or carboxy-terminal regions of Staphylokinase to engineer sites for PEG linkage to create new variants of staphylokinase. More specifically, the extended terminal regions of SAK carry one or more cysteine residues that allow SAK to make subunit association resulting in dimeric or multimeric state of SAK that display enhanced thermal stability and full biological activity comparable to its unmodified form.

The present invention also relates to covalent linkage of Polyethylene Glycol (PEG), ranging from 5 to 20 kDa of molecular weight, within the extended terminal region of SAK resulting in derivatives that display low protease sensitivity, higher thermal stability and extended plasma half life in vivo.

The present invention also relates to engineering of one or more cysteine residues within the extended region, specifically at the carboxy-terminal region, for PEG conjugation that can mask one of the antigenic sites (Lys135-Lys136) of SAK near the C-terminus and, thus, can reduce the antigenicity of protein resulting in a SAK derivative having increased stability, longer in vivo half life and reduced antigenicity.

The present invention, therefore, relates to engineered forms of SAK carrying amino and carboxy-terminal extension and their PEG conjugated variants that acquire new functions such as higher temperature stability, low protease sensitivity, reduced antigenicity and extended in vivo half life and, therefore, can have enhanced benefits in pharmaceutical composition for the treatment of various cardiovascular complications.

BACKGROUND

Staphylokinase is a profibrinolytic protein secreted by certain strains of *Staphylococcus aureus* that forms a stoichiometric complex with human plasminogen and displays localized plasminogen activation activity in a fibrin specific manner [Lack, C. H. (1948) Staphylokinase: an activator of plasma protease. Nature 161; Collen, D., De Cock, F., Vanlinthout, L, Declerck, P. J., Lijnen, H. R. and Stasen, J. M. (1992) Comparative thrombolytic and immunogenic properties of staphylokinase and streptokinase. Fibrinolysis 6; 232-242; Collen D., Lijnen, H. R. (1993) On the future of thrombolytic therapy for acute myocardial infarction. Am J Cardiol. 72; 46-50]. This is due to its ability to bind plasmin at the clot surface with nearly 150-fold higher affinity than the circulating plasminogen [Sakharov, D. V., Lijnen, H. R. and Rijken, D. C. (1996) Interaction between plasmin(ogen) and fibrin. J. Biol. Chem. 271; 27912-27918] where staphylokinase:plaminogen complex is rapidly inhibited by the blood component alpha 2-antiplasmin. In a clot environment plasminogen is partially degraded which results in conformational changes whereby binding with staphylokinase becomes stronger, therefore, resulting in a highly localized plasminogen activation activity around thrombi [Collen, D., De Cock, F., Vanlinthout, I., Declerck, P. J., Lijnen, H. R. and Stasen, J. M. (1992) Comparative thrombolytic and immunogenic properties of staphylokinase and streptokinase. Fibrinolysis 6; 232-242; Collen D., Wen, H. R. (1993) On the future of thrombolytic therapy for acute myocardial infarction. Am J Cardiol. 72; 46-50]. Since staphylokinase has a weak affinity for circulating but a high affinity for fibrin-bound plasminogen [Sakharov, D. V., Lijnen, H. R. and Rijken, D. C. (1996) Interaction between plasmin(ogen) and fibrin. J. Biol. Chem. 271; 27912-27918] it offers an advantage as a potential clot-dissolving agent with greater fibrin-specificity, considerably reduced antigenicity, and an efficacy at least as good as t-PA in terms of arterial patency [Vanderschueren S, Stockx L, Wilms G, Lacroix H, Verhaeghe R, Vermylen J, Collen D. (1995) Thrombolytic therapy of peripheral arterial occlusion with recombinant Staphylokinase. Circulation 92; 2050-2057; Vanderschueren, S., Van Vlaenderen, I. and Collen, D. (1997) Intravenous thrombolysis with recombinant staphylokinase versus tissue type plasminogen activator in a rabbit embolic stroke model. Stroke 28; 1783-1788].

Staphylokinase is a single chain 16 kDa protein, consisting of 136 amino acid residues. It forms a bimolecular complex with the blood proteins, such as plasminogen (PG) and plasmin (Pm) and exerts its fibrinolytic effects through conversion of an active non-specific serine protease, plasmin (Pm) to a highly specific proteolytic enzyme that can recognize blood zymogen, PG, as a substrate and convert it into plasmin that is capable of degrading blood clots. In a plasma milieu, SAK is able to dissolve fibrin clots without any associated fibrinogen degradation [Lijnen H. R., Van Hoef B., De Cock F., Okada K., Ueshima S., Matsuo O., Collen D. (1991) On the mechanism of fibrin-specific plasminogen activation by staphylokinase. J Biol. Chem. 266; 11826-11832; Collen D., Lijnen, H. R. (1993) On the future of thrombolytic therapy for acute myocardial infarction, Am J Cardiol. 72; 46-50]. Clinical trials have shown that Staphylokinase is as effective as t-PA at achieving early perfusion in myocardial infarction patients and its utility in thrombolytic treatment has now been established by several limited clinical trials [Collen D., Lijnen, H. R. (1993) On the future of thrombolytic therapy for acute myocardial infarction. Am J Cardiol. 72; 46-50; Lijnen, H. R., Collen, D. (1996) Staphylokinase, a fibrin-specific bacterial plasminogen activator. Fibrinolysis, 10; 119-126].

Staphylokinase is produced in very low amounts by its natural host, Staphylococcus aureus [Lack, C. H. (1948) Staphylokinase: an activator of plasma protease. Nature 161]. Considering its therapeutic applicability and clinical implications in thrombolytic therapy, several alternative sources of SAK production have been developed through recombinant routes. The staphylokinase gene has been cloned from the bacteriophages sakC [Sako, T., Sawaki, S., Sakurai, T, Ito, S., Yoshizawa, Y., Kondo, I. (1983) Cloning and expression of the staphylokinase gene of Staphylococcus aureus in Escherichia coli. Mol. Gen. Genet. 190; 271-277) and sak42D (Schlott, B., Hartmann, M., Guhrs, K. H., Birch-Hirschfeild, E., Pohl, H. D., Vanderschueren, S., van de Werf, F., Michoel, A., Collen, D. and Behnke, D. (1994) High yield production and purification of recombinant staphylokinase for thrombolytic therapy, Biotechnology 12; 185-189] as well as from the genomic DNA of a lysogenic Staphylococcus aureus strain [Behnke, D., Gerlach, D, (1984) Cloning and expression in Escherichia coli, Bacillus subtilis and Streptococcus sanguis of a gene for staphylokinase, a bacterial plasminogen activator. Mol. Gen. Genet. 210; 528-534]. The staphylokinase gene encodes a protein of 163 amino acids, with amino acid 28 corresponding to the NH2-terminal residue of full-length mature staphylokinase. The gene encoding for SAK has been overexpressed into various heterologous hosts, e.g., E. coli, Bacillus and Yeast [Sako, T., Sawaki, S., Sakurai, T, Ito, S., Yoshizawa, Y., Kondo, L (1983) Cloning and expression of the staphylokinase gene of Staphylococcus aureus in Escherichia coli. Mol, Gen. Genet. 190; 271-277; Behnke, D., Gerlach, D. (1984) Cloning and expression in Escherichia coli, Bacillus subtilis and Streptococcus sanguis of a gene for staphylokinase, a bacterial plasminogen activator. Mol. Gen. Genet. 210; 528-534; Schlott, B., Hartmann, M., Guhrs, K. H., Birch-Hirschfeild, E., Pohl, H. D., Vanderschueren, S., van de Werf, F., Michoel, A., Collen, D. and Behnke, D. (1994) High yield production and purification of recombinant staphylokinase for thrombolytic therapy. Biotechnology 12; 185-189] to produce SAK in large quantity in purified form for testing its clinical applicability.

Currently, attempts are being made to commercialize Staphylokinase for clinical use after several successful clinical and animal trial studies [Vanderschueren, S., Barrios, L., Kerdsinchai, P., Van den Heuvel, P., Hermans, L., Vrolix, M., De Man F., Benit, E, Muyldermans, L., Collen, D., Van de Werf, F., (2001) A randomized trial of recombinant staphylokinase versus alteplase for coronary artery patency in acute myocardial infarction. Circulation 92; 2044-2049; Armstrong, P. W., Burton, J., Pakola, S., Molhoek, P. G., Betriu, A. Tendera, M., Bode, C., Adgey, A. A., Bar, F., Van de Well, F. (2003) Collaborative Angiographic Patency Trial of Recombinant Staphylokinase (CAPTORS II). Am Heart J 146; 484-488]. However, being a product of bacterial origin, Staphylokinase elicits considerable allergic response during drug administration [Collen, D., De Cock, F., Vanlinthout, I., Declerck, P. J., Lijnen, H. R. and Stasen, J. M. (1992) Comparative thrombolytic and immunogenic properties of staphylokinase and streptokinase. Fibrinolysis 6; 232-242]. Attempts have been made to reduce its anitigenicity through the development of various mutant forms of Staphylokinase [Collen, D. (1996) Fibrin-selective thrombolytic therapy for acute myocardial infarction. Circulation 93; 857-865] where distinct mutations were created within its antigenic epitopes. Another limiting factor of Staphylokinase, that can hamper its use in thrombolytic therapy, is its relatively short plasma half-life (3-4 min) due to that repeated dose of this drug might be required to get effective recanalization during thrombolytic therapy and that in turn might exert higher allergic response in the patients. Therefore, development of second-generation SAK derivatives, where these shortcomings of native SAK are eliminated, would prove more advantageous. To overcome these problems, derivatives of SAK carrying PEG attachment within the protein at various sites have been generated [Vanwetswinkel, S., Plaisance, S., Zhi-Yong, Vanlinthout, I., Brepoels, K., Lasters, I., Collen, D., and Jespers, L. (2000) Pharmacokinetic and thrombolytic properties of cysteine-linked polyethylene glycol derivatives of staphylokinase. Blood. 95; 936-942; Verhamme, P., Goossens, G., Maleux, G., Collen, D. and Stas, M. (2007) A dose-finding clinical trial of staphylokinase SY162 in patients with long-term venous access catheter thrombotic occlusion. J Thromb Thrombolysis. 24; 1-5], however, derivatives carrying PEG at internal sites displayed significantly lower specific activity [Vanwetswinkel, S., Plaisance, S., Zhi-Yong, Vanlinthout, I., Brepoels, K., Lasters, I., Collen, D., and Jespers, L. (2000) Pharmacokinetic and thrombolytic properties of cysteine-linked polyethylene glycol derivatives of staphylokinase. Blood, 95; 936-942] suggesting internal sites within the core region of SAK may not be suitable for the chemical modification of SAK.

Cysteine derivatives of Staphylokinase have been described in the prior art [Vanwetswinkel, S., Plaisance, S., Zhi-Yong, Vanlinthout, I., Brepoels, K., Lasters, I., Collen, D., and Jespers, L. (2000) Pharmacokinetic and thrombolytic properties of cysteine-linked polyethylene glycol derivatives of staphylokinase. Blood. 95; 936-942; U.S. Pat. No. 6,383,483 "Staphylokinase derivatives with cysteine substitutions"; U.S. Pat. No. 6,902,733 "Staphylokinase derivatives with polyethylene glycol"] where cysteine residue has been substituted within the core region and amino-terminal part of Staphylokinase. Derivatization of cysteine substituted SAK mutants with PEG within the core region resulted in substantial loss of its plasminogen activation ability. Therefore, ideal site for the PEG conjugation within the core region has not been found and the approach to conjugate PEG with SAK has not been successful as these SAK derivatives display significantly lower plasminogen activation ability than the native form of SAK. Recombinant Staphylokinase variants obtained by site-directed substitution with cysteine, within the NH2-terminal region of SAK (serine 2 [Ser2] and/or Ser3), that is released from the core of the protein during plasminogen activation process, were derivatized with thiol-specific (ortho-pyridyl-disulfide or maleimide) polyethylene glycol (PEG) molecules, resulting in a SAK derivative that displayed a plasma half-life 4-5 fold higher (~13 min) than the unmodified form (>3 min). The specific activity and thrombolytic potency of this SAK derivative in human plasma was found comparable to that of native SAK and currently this SAK variant is under clinical trial [Verhamme, P., Goossens, G., Maleux, G., Collen, D. and Stas, M. (2007) A dose-finding clinical trial of Staphylokinase SY162 in patients with long-term venous access catheter thrombotic occlusion. J Thromb Thrombolysis. 24; 1-5]. Although circulating half-life of PEG-linked SAK derivatives, described in the known literature or disclosed in known patents [Johnson, C., Royal, M., Moreadith, R., Bedu-Addo, F., Advant, S., Wan, M., and Conn, G. (2003) Monitoring manufacturing process yields, purity and stability of structural variants of PEGylated staphylokinase mutant SY161 by quantitative reverse-phase chromatography. Biomed Chromatogr. 17; 335-344] have been claimed to increase to certain extent, their use as a single bolus injection for clinical intervention, might require further improvement in the stability and half life of SAK molecule. The engineering of SAK for further improvement has been limited due to its smaller size and difficulty in targeting specific regions of protein without compromising functional properties of SAK as most of the regions of either involved in the interaction with the partner plasmin(ogen) or substrate plasminogen [Parry, M. A., Fernandez-Catalan, C., Bergner, A., Huber, R., Hopfner, K. P., Scholott, B., Guhrs, K. H. Bode, W (1998). The ternary microplasmin-staphylokinase-microplasmin complex is a protease-cofactor-substrate complex in action. Nat. Struct. Biol. 10; 917-923].

The present invention, therefore, unravels a novel strategy for engineering a SAK molecule to improve its thrombolytic properties by enhancing its plasma half life and stability and a low immune reactivity. The said properties are achieved although their clot dissolving ability is maintained similar to that of the wild type molecule. Here, design and development of new SAK derivatives has been discussed where amino and/or carboxy terminal regions of SAK have been extended by introducing new amino acid sequences, particularly one or more cysteine residues, to create dimeric/multimeric forms of SAK, and their modification by attaching a PEG molecule of different sizes within the extended region so that the integrated PEG with SAK remains away from the core functional region and does not interfere with biological function of SAK but simultaneously can increase overall stability and shelf life of the protein. Moreover, the Staphylokinase derivatives, thus generated, can have extended in vivo plasma half-life, thus, creating new SAK mutants that can be more advantageous in thrombolytic therapy. In principal, the present invention, disclosed herein, relates to new derivatives of Staphylokinase displaying higher thermal stability and increased in-vivo half-life than the unmodified Staphylokinase.

Therefore, details disclosed in the present invention, provide new strategy and design for the modification of SAK for engineering and chemical modification of SAK for enhancing its thrombolytic potential. SAK derivatives, thus generated, having multimeric forms and/or conjugated with PEG, disclosed in the present invention, display significant improvement in their functional properties over an unmodified SAK form and other known derivatives with respect to stability and circulating half-life and can be more useful for clinical purposes for the treatment of cardiovascular complications providing the advantage of higher temperature stability that can increase the shelf life of the protein and extended half life that can reduce the requirement of repeated dose during thrombolytic therapy.

The prime objective of the present invention is to develop a cysteine variant of Staphylokinase wherein at least one cysteine residue is added at amino and carboxy-terminal extension of SEQ ID NO: 1.

Another object of the present invention is to develop biologically functional derivatives of SAK that can display higher thermal and protease stability so that the shelf life of protein is increased and its plasma half-life in vivo is extended so that it can be more beneficial for the thrombolytic therapy. Integration of these two attributes in a SAK molecule can tremendously increase therapeutic potential of Staphylokinase for the treatment of circulatory disorders.

The other objective of the present invention is to extend amino and/or carboxy terminal regions of SAK carrying one or more cysteine residues to alter subunit association properties of SAK and to conjugate different lengths of PEG molecule away from the main functional regions of protein so that biological activity of protein is not compromised after PEG attachment but simultaneously can provide protection to the molecule from the protease attack so that its circulating half life in vivo is extended.

Yet another objective of the invention is to prepare a piece of DNA carrying complete genetic information for the production of SAK derivatives in a suitable host such as *E. coli, Bacillus*, Yeast or any microbial system using known recombinant DNA techniques for high level intracellular production of various SAK derivatives so that large amount of SAK mutant proteins can be obtained in high yield.

Yet another objective of the invention is to prepare SAK derivatives in purified form using known protein purification techniques and then conjugate one or more PEG molecule within the extended region of SAK to prepare mono or di PEGylated forms of SAK.

Overall objective of the present invention, therefore, is to develop new derivatives of SAK that can display better stability, enhanced shelf life and extended plasma half-life in vivo. These attributes in the staphylokinase derivatives, disclosed herein, will significantly improve thrombolytic potential of staphylokinase for the treatment of cardiovascular disorders.

BRIEF SUMMARY

Accordingly, the present invention provides a cysteine variant of Staphylokinase (a Staphylokinase variant) wherein at least one cysteine residue is added at amino and carboxy-terminal extension of SEQ ID NO:1. In one embodiment, the at least one cysteine residue is added to the N-terminal region of SEQ ID NO:1 by substituting at least one amino acid residue in the N-terminal region of SEQ ID NO:1 with the at least one cysteine residue. In another embodiment, the at least one cysteine residue is added to the N-terminal region of SEQ ID NO:1 by adding the at least one cysteine residue to the N-terminal amino acid of SEQ ID NO:1. In another embodiment, the at least one cysteine residue is added to the C-terminal region of SEQ ID NO:1 by adding the at least one cysteine residue to the C-terminal amino acid of SEQ ID NO:1.

In an embodiment of the present invention, a cysteine variant of Staphylokinase is provided, wherein the cysteine variant of Staphylokinase comprises a sequence selected from the group consisting of SEQ ID NO:3, SEQ ID NO:4, SEQ ID NO:5 and SEQ ID NO:6. In another embodiment, the cysteine variant of Staphylokinase consists of a sequence selected from the group consisting of SEQ ID NO:3, SEQ ID NO:4, SEQ ID NO:5 and SEQ ID NO:6

In an embodiment of the present invention, a cysteine variant of Staphylokinase wherein one or more cysteine residues are added to the regions comprising of before N-terminal amino-acid of Staphylokinase polypeptide, after the C-terminal amino-acid of Staphylokinase polypeptide. In one embodiment, one or more cysteine residues are added to the N-terminal residue of SEQ ID NO:1. In another embodiment, the one or more cysteine residues is added to the C-terminal residue of SEQ ID NO:1.

In another embodiment of the present invention, a cysteine variant of Staphylokinase, wherein cysteine variant has N and/or C-terminus extension of amino-acids.

In another embodiment of the present invention, a cysteine variant of Staphylokinase wherein the substituted cysteine residue is modified with a cysteine-reactive moiety.

In yet another embodiment of the present invention, a cysteine variant of staphylokinase is provided, wherein at least one or more substituted or added cysteine residue is modified with or conjugated to a polyethylene glycol (PEG) molecule.

In yet another embodiment of the present invention, the PEG molecule attached to the PEGylated cysteine variant is a linear or branch polymer of molecular size ranging from 5-20 Kilodaltons.

In still another embodiment of the present invention, the PEGylated cysteine variant has increased proteolytic stability as compared to their original unmodified counterparts. In yet another embodiment, the Staphylokinase variant has proteolytic stability greater than the proteolytic stability of SEQ ID NO:1.

In still another embodiment of the present invention, the PEGylated cysteine variant, wherein said variant has decreased antigenicity and in vivo immunogenicity when compared to their original unmodified counterparts. In yet another embodiment, the Staphylokinase variant has in vivo immunogenicity which is less than the in vivo immunogenicity of SEQ ID NO:1.

In still another embodiment of the present invention, the PEGylated cysteine variant, wherein said variant has slow renal clearance hence increased in vivo half life as compared to their original unmodified counterparts. In yet another embodiment, the Staphylokinase variant has an in vivo half life which is greater than the in vivo half life of SEQ ID NO:1.

In still another embodiment of the present invention, a cysteine variant of staphylokinase wherein SAK derivatives and their PEG conjugated forms display higher temperature stability ranging from 20° C. to 80° C. than their unmodified form and wild type SAK.

In still another embodiment of the present invention, a cysteine variant of staphylokinase wherein the extended carboxy-terminal end of staphylokinase carries a single cysteine residue and the plasmid DNA encoding this SAK variant (SAK 1C-CT), has been transformed into an *E. coli* host to express this SAK derivative.

In still another embodiment of the present invention, the recombinant *E. coli* strain has been deposited in International Depository (IDA) section of Microbial type culture collection under designation of MTCC 5437.

In still another embodiment of the present invention, a cysteine variant of staphylokinase wherein the carboxy terminal region of staphylokinase derivative carry two cysteine residues and a plasmid DNA encoding this SAK variant (SAK 2C-CT) has been transformed into an *E. coli* host to express this SAK derivative.

In still another embodiment of the present invention, the recombinant *E. coli* strain has been deposited in International Depository (IDA) section of Microbial type culture collection under designation of MTCC 5438.

In still another embodiment of the present invention, a cysteine variant of staphylokinase wherein the extended amino-terminal end of staphylokinase carries a single cysteine residue and the plasmid DNA encoding this SAK variant (SAK 1C-NT) has been transformed into an *E. coli* host to express this SAK derivative.

In still another embodiment of the present invention, the recombinant *E. coli* strain has been deposited in International Depository (IDA) section of Microbial type culture collection under designation of MTCC 5439.

In further embodiment of the present invention, a cysteine variant of staphylokinase wherein the extended amino-terminal region of staphylokinase derivative carries two cysteine residues and a plasmid DNA encoding this SAK variant (SAK 2C-NT) has been transformed into an *E. coli* host to express this SAK derivative.

In further embodiment of the present invention, the recombinant *E. coli* strain has been deposited in International Depository (IDA) section of Microbial type culture collection under designation of MTCC 5440.

In one embodiment of the present invention, a vector comprising a DNA molecule encoding SEQ ID NO:3, SEQ ID NO:4, SEQ ID NO:5 or SEQ ID NO:6 is provided.

In one embodiment, a recombinant *E. coli* host cell having a vector comprising a DNA molecule encoding SEQ ID NO:3, SEQ ID NO:4, SEQ ID NO:5 or SEQ ID NO:6 is provided.

In yet further embodiment of the present invention, a pharmaceutical composition comprising at least one of the pegylated derivatives together with, or without, excipient(s).

In yet further embodiment of the present invention, a pharmaceutical composition, for treating circulatory disorder selected from the group consisting of myocardial infarction, vascular thromboses, pulmonary embolism, stroke a vascular event, disease or disorder selected from a group consisting of myocardial infarction, angina, pulmonary embolism, transient ischemic attack, deep vein thrombosis, thrombotic re-occlusion subsequent to a coronary intervention procedure, heart surgery or vascular surgery, peripheral vascular thrombosis, Syndrome X, heart failure, and a disorder in which a narrowing of at least one coronary artery occurs.

BRIEF DESCRIPTION OF THE DRAWINGS

FIG. 2. Pegylation of SAK mutants carrying amino and carboxy terminal extension. Integration of PEG molecule with SAK was analyzed by running Pegylated forms of SAK derivatives on 10% SDS-PAGE before and after purification.

DETAILED DESCRIPTION

Figure 1:
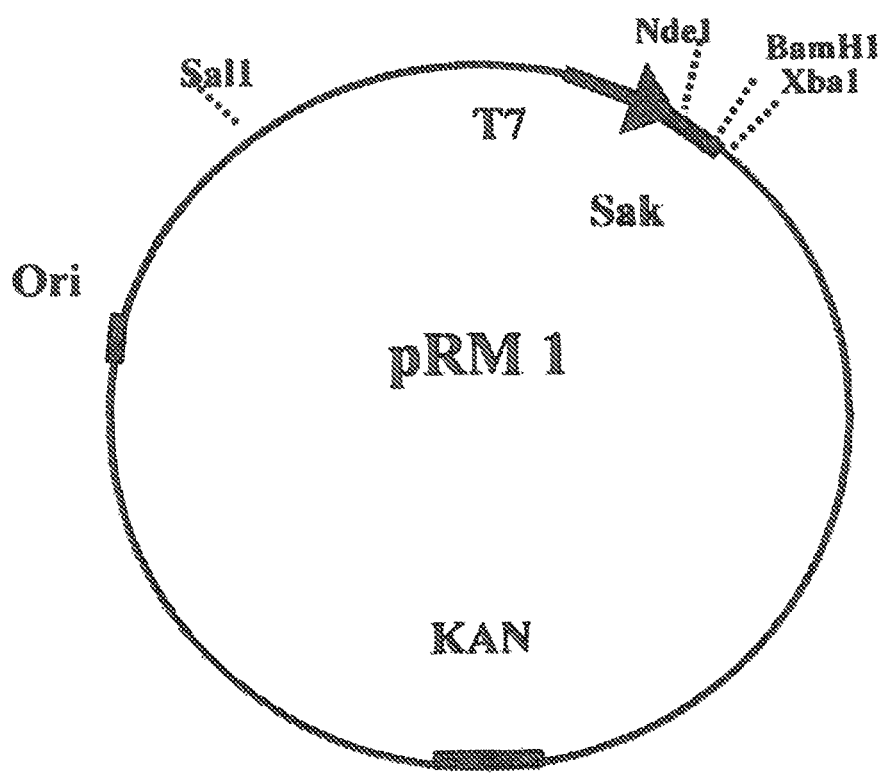
FIG. 1. Restriction map of recombinant plasmid pRM1 showing site of integration of a SAK encoding gene.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art.

All publications, patents and patent applications cited herein, whether supra or infra, are hereby incorporated by reference in their entirety.

The present invention provides a cysteine variant of Staphylokinase wherein at least one cysteine residue is added at amino and carboxy-terminal extension of SEQ ID NO: 1.

The invention also pertains to new derivatives of stapylokinase carrying extended amino and carboxy terminal ends where one or more cysteine residues were introduced to modify oligomeric state of protein, resulting in staphylokinase mutants displaying enhanced thermal stability. The variants, carrying cysteine residue(s) at one or both ends of polypeptide, were further modified by conjugation of PEG molecule, ranging from 5 to 20 kDa, to enhance proteolytic resistance and plasma half life of Staphylokinase.

The present invention also relates to peptide sequence of Staphylokinase having SEQ ID NO:1, its corresponding gene with nucleotide sequence given in SEQ ID NO:2, or mutants or derivatives thereof developed using known procedures, their expression in a heterologous host, e.g., E. coli, Bacillus, Yeast, their production and purification in large amount using general methods of recombinant DNA and protein purification, covalent modification of mutant polypeptides by conjugating PEG molecule of different sizes. SAK derivatives, thus created, display enhanced thermal and protease stability and extended in vivo retention.

The present invention also pertains to covalent modification of SAK with PEG attachment to mask one of the antigenic sites without affecting biological activity so that resulting molecule can have reduced antigenicity.

The present invention also pertains to the pharmaceutical use of Staphylokinase derivatives and their PEG conjugated forms along with suitable composition of carriers and stabilizers for clinical administration in the body for the treatment of cardiovascular diseases. The invention also relates to modified polypeptides carrying amino acid sequence of SEQ ID NOs. 3, 4, 5 and 6 and their encoding gene sequences for modified Staphylokinase derivatives, as well as their respective expression plasmids ligated with these mutant SAK-encoding nucleic acid sequences. E. coli host cells transformed with the plasmids encoding the Staphylokinase derivative proteins were deposited with the International Deposition Authority (IDA) section of Microbial type culture collection and were assigned deposit numbers MTCC 5437 (SAK 1C-CT, SEQ ID NO:5), MTCC 5438 (SAK 2C-CT, SEQ ID NO:6), MTCC 5439 (SAK 1C-NT, SEQ ID NO:3), and MTCC 5440 ((SAK 20-NT, SEQ ID NO:4), and are capable of producing large amounts of mutant SAK proteins in the intracellular compartment of the recombinant E. coli cells. This invention further relates to a process for the purification of Staphylokinase derivatives and their further modification by covalent linkage of PEG outside the functional region of protein, particularly within the extended amino or carboxy terminal regions of SAK, and lastly, a method of dissolving blood clot in a subject in need thereof.

The invention discloses the integration of one or more amino acid residues, carrying one or multiple cysteines at amino and/or carboxy terminal regions of SAK using known genetic engineering techniques, creating SAK derivatives that are able to attain dimeric and multimeric forms and display higher stability than the unmodified form.

In a preferred embodiment, single and/or double cysteine residues are added at amino and/or carboxy-terminal region of SAK resulting in SAK derivatives showing higher protein stability than the unmodified form.

In another embodiment, SAK derivatives having one or more cysteine residue(s) within the extended region of SAK are produced into a suitable host such as E. coli, Bacillus, Yeast etc. using any recombinant DNA techniques known in the prior art and purified from the cell extract through various known protein purification techniques such as Ion Exchange Chromatography, Hydrophobic Interaction Chromatography, Gel filtration techniques etc.

In another preferred embodiment, purified protein preparation of SAK derivatives or their mutants are chemically modified to conjugate PEG molecule of 5, 10 or 20 kDa using known procedures.

The following examples are given by way of illustration of the present invention and therefore should not be construed to limit the scope of the present invention General Methods Utilized in the Example Recombinant DNA techniques: Conventional and well-known techniques of recombinant DNA and molecular biology were utilized. Details of these techniques are available in various standard text books or manuals related to this field for example, Sambrook et. al., Molecular Cloning: A Laboratory Manual (2nd edition, Cold spring Harbor Press, New York, 1989. The source of SAK gene for the purpose of modification is plasmid, pRM1 (as detailed in EP Patent No. 1608677 "A method for oxygen regulated production of recombinant Staphylokinase"). The SAK gene was engineered to extend amino and/or carboxy terminal ends following polymerase chain reaction (PCR) following standard protocols of generic engineering techniques [Sambrook J., Fritsch E. F., Maniatis T. (1989) Molecular cloning a laboratory manual. 2nd Ed. Cold Spring Harbor, N.Y. Cold Spring Harbor Laboratory Press] and mutant SAK genes were cloned on a T7 RNA polymerase based expression vector, pET9b and was transformed in the *Escherichia coli* BL21 DE3 strain obtained from New England Biolabs.

Electrophoretic analysis of proteins: Purified preparation of SAK or its presence in vivo was analysed through SDS-PAGE, essentially according to Laemmli procedure.

Casein-Plasminogen overlay assay for detection of SAK activity: Bacterial colonies producing Staphylokinase were detected by overlay of casein and human plasminogen in soft agar as mentioned by Behnke et al., 1984. Briefly, 10 ml of soft agarose mixture carrying 0.8% agarose, 10% skim milk, 100 mU of human plasminogen, 150 mM NaCl and 50 mM Tris-Cl (pH. 8.0) is poured on to top of the plates carrying bacterial colonies expressing staphylokinase. These plates were incubated at 37° C. for 4-5 h and SAK carrying colonies were identified by the presence of a clearing zone around the colonies. Biological activity of SAK protein can also be tested on plate overlayered with casein and human plasminogen after putting a spot of purified protein on the plate.

Assay for Staphylokinase mediated plasminogen activation using chromogenic peptide substrate. Plasminogen activation ability of Staphylokinase and its modified forms were checked through known procedures (Jackson, K. W., Esmon, N., Tang, J. (1981) Streptokinase and Staphylokinase, Methods enzymol. 80; 387-394). Briefly, 10 µl of appropriately diluted sample of SAK was mixed with 25 µl of sample buffer (50 mM Tris.Cl, pH 7.5) and 15 µl of human plasminogen (0.5 mg/ml) and incubated at 37° C. for 15 minutes and then 18 µl of NaCl (1.77 M in 50 mM Tris. Cl, pH 7.5) is added. The amount of plasmin thus generated was measured after addition of 12 µl of chromogenic substrate, Chromozyme PL (5 mg/ml in water, Boehringer Mannheim), and tubes were further incubated at 37° C. for 10 minutes. SAK activity was measured at 405 nm due to the release of yellow colored p-4-nitroaniline.

Clot lysis assay: Clot lysis ability of SAK or its modified forms was tested following the standard methods (British Pharmacopia, 1980 edition), Fibrin clot lysis was carried out in the presence of citrated human plasma or human fibrinogen containing different concentrations of SAK or its analogs. Briefly, fibrin clot was labeled by radioiodination (1-125) and mixed with appropriate concentrations of SAK and incubated at 37° C. and rotated slowly. 0.1 ml aliquot was removed at regular intervals and release of soluble fibrin was measured by the amount of radioactivity released using gamma counter.

Temperature stability: Stability of SAK derivatives or their PEG conjugated forms was determined by incubating the purified preparation of each derivative at 4° C., 37° C., 42° C. and 65° C. for different time periods and then testing their ability for the plasminogen activation using known standard technique mentioned above.

Proteolytic stability: Each SAK derivative or their PEG conjugated form was incubated with trypsin in the ratio of 1:100 and 1:200 at 37° C. and its degradation was analyzed on SDS-PAGE and also after checking their biological activity by casein-plasminogen assay after spotting on LB-Agar plate.

Determination of plasma half life of SAK derivatives: SAK derivatives and their PEG conjugated forms were labeled with 1125 (Perkin Elmer) using Iodogen (1,3,4,6-Tetrachloro-3a-6 alpha-diphenylglucoluril) method following standard procedure [Fraker, P. J., Speck, J. C. (1978) Protein and cell membrane iodination with a sparingly soluble choramide 1,3,4,6-tetrachloro-3a,6a-diphenylgylycoril. Biochem. Biophys. res. commun. 80; 849-857]. Iodinated SAK derivatives were injected into blood plasma as well as in live mice and samples were withdrawn at different time intervals to check the stability of SAK derivatives in blood plasma.

Immunogenicity of PEGylated cysteine derivatives of SAK: Immunological properties of various SAK cysteine derivatives was checked using SAK specific polyclonal antisera raised against WT SAK. Immunoreactivity of various PEGylated SAK derivatives and WT SAK was checked against this antibody by ELISA plate method. The microtitre plate was incubated at 4° C. overnight with SAK or PEGylated cysteine mutants containing 1 µg of protein in coating buffer i.e. 0.2 M bicarbonate buffer pH 9.2. The plate was washed with 2000 PBS-T three times. 100 µl of diluted (1:40000 in PBS) primary antibody against SAK was added to each well and incubated at 37° C. for 4 hrs. After three washings, 100 µl of HRP conjugated antibody was added in 1:5000 dilution and kept for 1 hr at 37° C. The plate was washed three times with PBS. 100 µl of TMB substrate was added to each well and incubated for 20-30 min at 37° C. Finally 50 µl of H2SO4 was added to stop the reaction and the plate was read at 450 nm. The immmunoreactivity of SAK and different PEGylated derivatives was evaluated by comparing the absorbance values at 405 nm.

EXAMPLES

The following examples illustrate certain aspects and advantages of the present invention, however, the present invention is in no way considered to be limited to the particular embodiments described below.

Example 1

Construction of SAK mutants carrying extended amino and carboxy terminal regions: SAK is the smallest known protein that has an efficient plasminogen activator activity. Major portion of SAK polypeptide is important for either forming a bimolecular complex with plasminogen or interaction with a substrate molecule. Therefore, addition or a deletion within the core region of SAK often results [Schlott, B., Gurhs, H. K., Hartmann, M., Rocker, A., Collen, D. (1997) Staphylokinase requires NH2-terminal proteolysis for plasminogen activation. J. Biol. Chem, 273; 22346-22350; Rajamohan, G. and Dikshit, K. L. (2000) Role of the N-terminal region of Staphylokinase (SAK) evidence for the participation of the N-terminal region of SAK in the enzyme-substrate complex formation. FEBS Lett. 474; 151-158] in a non-functional form of protein. Therefore, to generate derivatives of SAK, extension of one or more amino acid residues carrying one or multiple cysteine residues at terminal positions, was done using recombinant DNA techniques so that this region can be targeted for engineering new attributes to the protein. Amino or carboxy-terminal extension of SAK was done by polymerase chain reaction using oligonucleotide primers and extension of SAK was done at both the ends either individually or in combination. Table 1 shows the amino acid sequences of first or last seven residues of SAK derivatives. PCR amplified product of each SAK derivative was cloned on an expression vector pET 9b. Primary recombinant plasmid, pRM1 has been described earlier (EP Patent No. 1608677 "A method for oxygen regulated production of recombinant Staphylokinase"; US patent pending). Map of this recombinant plasmid is given in FIG. 1, The nucleotide sequence of each SAK derivative was confirmed through automated DNA sequencing (Applied Biosystems). Details of amino acid and nucleotide sequence of wild-type SAK are given in SEQ ID NO:1 and SEQ ID NO:2, respectively.

Amino acid sequence of SAK derivatives is shown in the sequence listing.

centrifuged at 6000.times.g at 4° C. for 15 min and clear lysates were diluted two fold with 10 mM Tris.Cl buffer and thereafter applied at room temperature to a 10 times 32 cm column of SP-sepharose at a flow rate of 1 liter per hour. The column was washed with 10 mM Tris.Cl buffer, pH 6.2 and eluted with a gradient of 0.1 to 0.5 M NaCl. The SAK containing fraction was checked by spot test by mixing 1 μl fraction with 1 mU of human plasminogen (0.5 mg/ml) and 1 mU of chromozyme PL. The SAK containing fractions exhibited development of yellow color. These fractions were pooled and adjusted to 2.5 M with solid sodium chloride and subjected to hydrophobic interaction chromatography on a 10.times.20 cm column of phenyl-sepharose at room temperature and flow rate of 1 liter/hour. The column was washed with 0.1 M phosphate buffer and SAK was eluted

TABLE 1

Staphylokinase Derivatives Carrying Extended Amino and for Carboxy Terminals

| SAK Derivatives | Extended Region | Sequence of First or Last 7 Amino Acid Residues |
|---|---|---|
| SAK WT (SEQ ID NO: 1) | None | SSSFDKG (N-terminus) KVVIEKK (C-terminus) |
| S3C (SEQ ID NO: 7) | None (cysteine residue substituted with serine at 3$^{rd}$ position of amino terminal region) | SSCFDKG |
| SAK 2CNT (SEQ ID NO: 4) | Two cysteine residues added at the N-terrninal region of SAK | CCSSSFD |
| SAK 1CNT (SEQ ID NO: 3) | One cysteine residue added at the N-terminal region of SAK | CSSSFDK |
| SAK 2CCT (SEQ ID NO: 6) | Two cysteine residues added at the carboxy-terrninal region of SAK | VIEKKCC |
| SAK 1CCT (SEQ ID NO: 5) | One cysteine residue added at the carboxy-terminal region of SAK | VIEKKAC |

Example 2

Intracellular production of SAK derivatives and their recovery from recombinant E. coli: E. coli cells transformed with recombinant plasmid carrying mutant SAK gene were streaked on a Luria Bertani (LB) agar plate containing 50 μg/ml Kanamycin and kept in an incubator set at 37° C. for overnight. Individual colonies appearing on the plate were used to raise seed culture in a 10 ml liquid LB medium supplemented with 50 μg/ml Kanamycin and grown at 37° C., 200 rpm on a gyratory shaker for 8-10 h. This primary seed culture (1% v/v) was used to inoculate 1 liter of LB medium containing 50 μg/ml Kanamycin and allowed to grow at 37° C. at 200 rpm till its optical density (00600 nm) reaches to 0.4-0.5. The culture was then induced for SAK production by adding 0.1 mM IPTG and further grown at 37° C. for another 6-8 hours. Cells were then harvested by spinning them down by centrifugation at 6000.times.g in a GS-3 rotor (Sorvall) for 30 min at 4° C. The supernatants were discarded and the cell pellet was resuspended in 15 ml of 10 mM Tris.Cl buffer and lysed either by sonication or chemical lysis using 6M-guanidium hydrochloride and 20 mM sodium phosphate buffer, pH 7.2. The cell lysate was with 0.01 M phosphate buffer (pH 6.2). Aliquots from each fraction were analyzed on 15% SDS-PAGE to examine the relative purity of the eluted protein. On SDS-PAGE, it showed a single band of 16 kDa. Table 2 shows the specific activity of SAK and its derivatives by standard procedure of plasminogen activation assay.

TABLE 2

Functional Properties of SAK Derivatives

| SAK Derivatives | Specific Activity (U/mg) |
|---|---|
| SAK WT* | 67 U/mg |
| SAK (Recombinant) | 66 ± 3.5 U/mg |
| SAK S3C | 60 ± 4.1 U/mg |
| SAK 1CNT | 40 ± 4.3 U/mg |
| SAK 2CNT | 57 ± 3 8 U/mg |
| SAK 1CCT | 64 ± 4.5 U/mg |
| SAK 2CCT | 65 ± 3.8 U/mg |

*WT SAK with 67 U/mg was obtained from World Health Organization and used as a standard to compare specific activity of SAK derivatives.

Example 3

Determination of sub-unit association properties of SAK derivatives: In order to check how the extension of amino terminal regions of SAK and placement of cysteine residues within this region has affected the oligomeric state of protein, purified preparation of each SAK derivative was run on a native 10% polyacrylamide gel without adding any SDS and mercaptoethanol. Gel was stained with coomassie blue to check change in the oligomeric state of the protein. Checking the molecular mass of each SAK derivative following standard method of size exclusion chromatography on a G75 Sephadex column further substantiated change in the oligomeric state of protein.

Example 4

Conjugation of Polyethylene Glycol with SAK derivatives extended at amino and carboxy terminal regions: Maleimide activated methoxy Polyethylene Glycol of different sizes 5, 10, 20 kDa was used to conjugate PEG molecule with SAK derivatives carrying single or multiple cysteine residues within their extended amino or carboxyl ends. Initially, different molar ratio of SAK derivative and PEG (ranging from 1:2 to 1:5) were mixed in a pegylation reaction buffer (comprising of 50 mM Tris.Cl (pH 8.0), 100 mM NaCl) and kept at room temperature for different time periods to find out the ideal condition for PEG linkage with individual SAK derivative. Particularly in the case of SAK derivative carrying more than one cysteine, condition for the PEG linkage has been optimized by standardizing the ratio of protein and PEG as well as time of incubation so that all cysteine residues can be pegylated maximally. Passing through the Amicon column having 15 kDa cut off then separated unlinked PEG molecule from the protein. Mono and dipegylated form of protein were separated through size exclusion chromatography on a Superdex G 75 column through protein purification system linked with online data recording (Acta Prime, Amersham Biosciences).

Figures 2A, 2B:
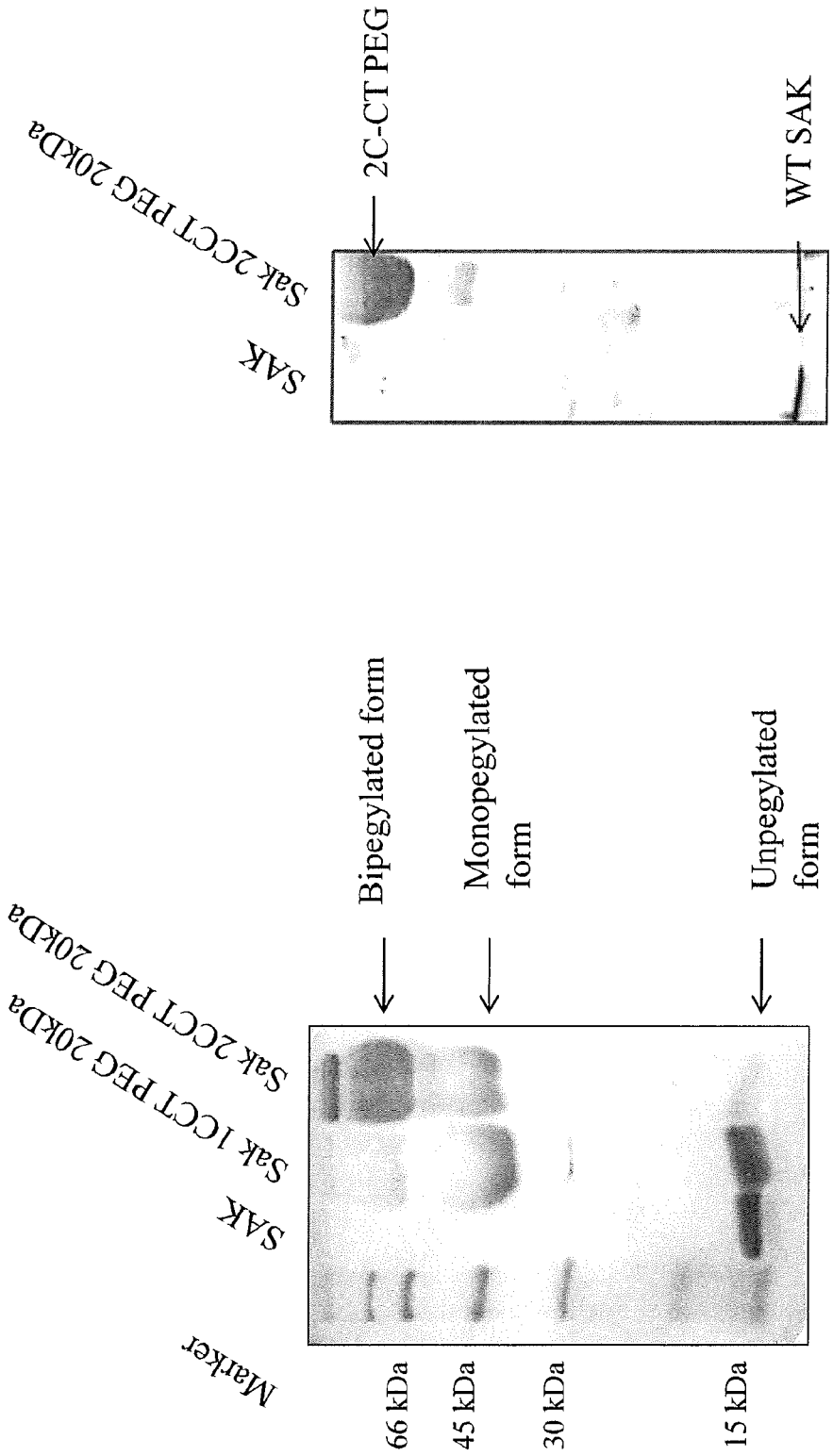
FIG.2A shows that SAK derivative carrying one cysteine residue at C-terminus end displayed only monopegylated form and SAK derivative carrying two cysteine residues at C-terminus end displayed monopegylated and bipegylated forms along with some unpegylated form.
FIGS. 2B and 2C show the purified derivatives of Pegylated SAK 2CCT and SAK 1CCT with conjugated PEG 20 kDa respectively.
Figures 2C, 2D:
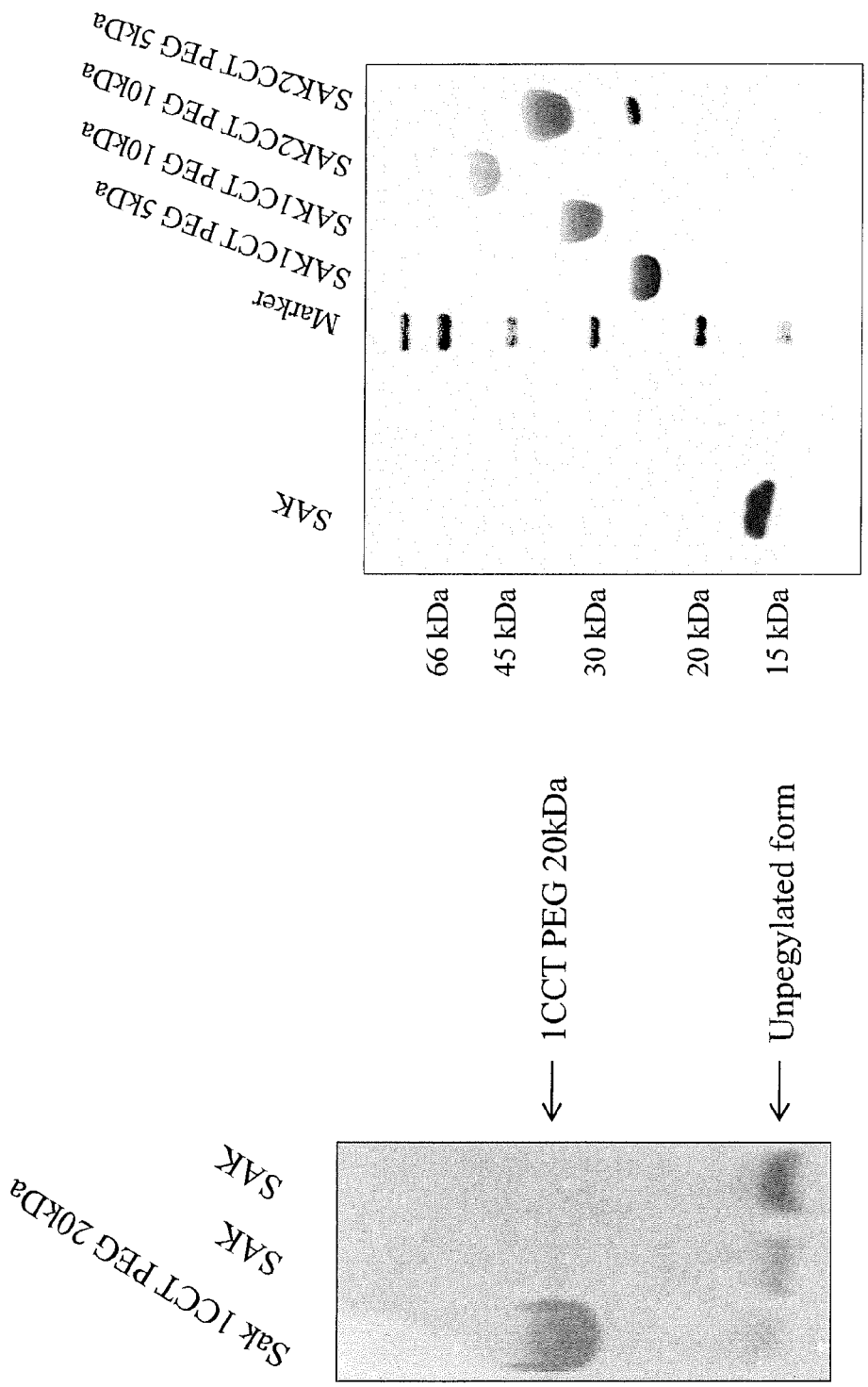
FIG. 2D shows purified derivatives of SAK 1CCT and SAK 2CCT with conjugated 5 kDa and 10 kDa PEG molecules as labeled.

Integration of PEG molecule with SAK was checked by analyzing the Pegylated forms of SAK derivatives on 10% SDS-PAGE. SAK derivative carrying cysteine residue at one end displayed only monopegylated form along with some unpegylated form as shown in FIG. 2. efficiency of SAK mutants to form mono and dipegylated forms were different in each case (FIG. 2).

Example 5

Figure 3:
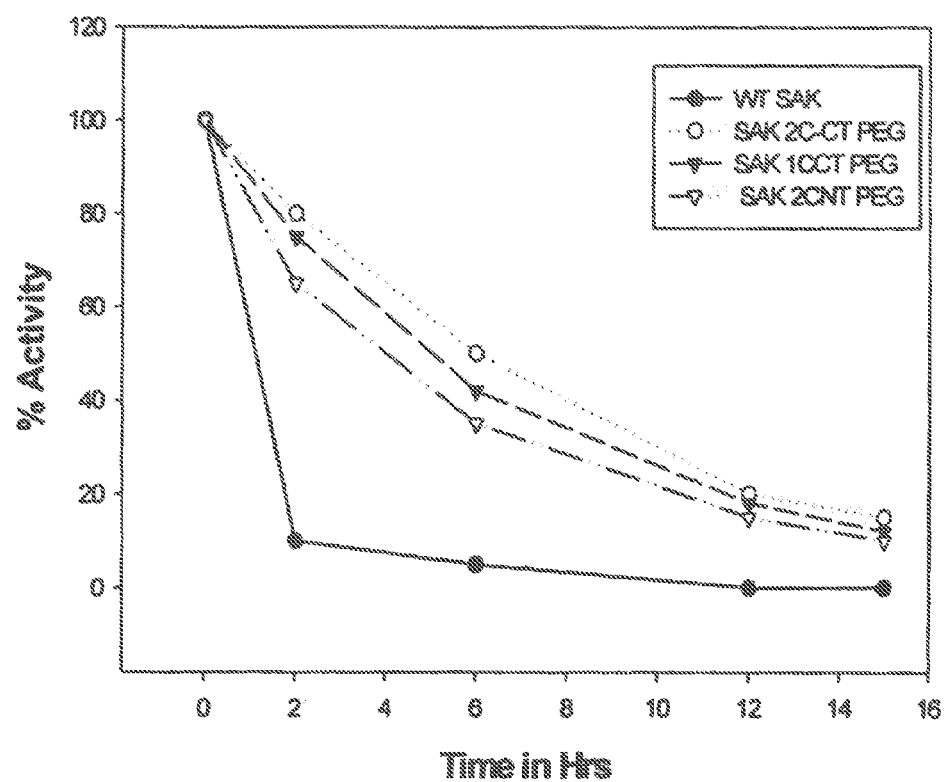
FIG. 3. Stability of various SAK derivatives at 65° C.

Temperature stability of SAK derivatives and their PEG conjugated forms: PEG conjugated forms of different SAK derivatives were purified after Gel-filtration column using standard biochemical procedure and concentrated. 200 μl of purified protein preparation of SAK derivatives and their PEG linked forms were kept at 4° C., 37° C., 42° C. and 65° C. at concentration 1 mg/ml in 50 mM tris buffer (pH 7.5) and aliquot of 10 μl was removed at different time intervals and their residual functional activity was checked by testing their plasminogen activator activity. Stability profile of different SAK variants at 65° C. is shown in FIG. 3.

Example 6

Figure 4:
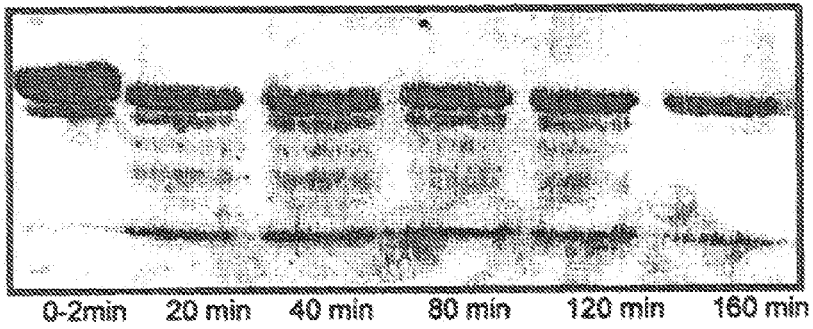
FIG. 4. Trypsin digestion profile of SAK and PEGylated derivatives of SAK.
Figure 4:
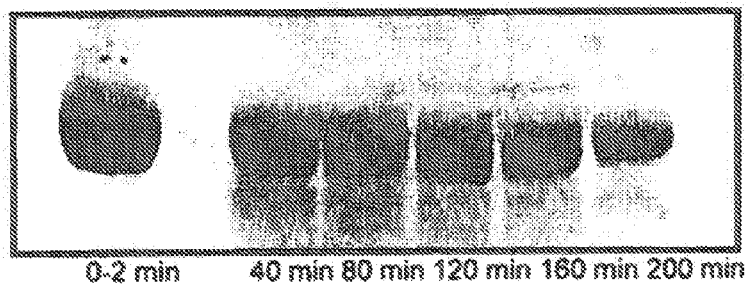
Figure 4:
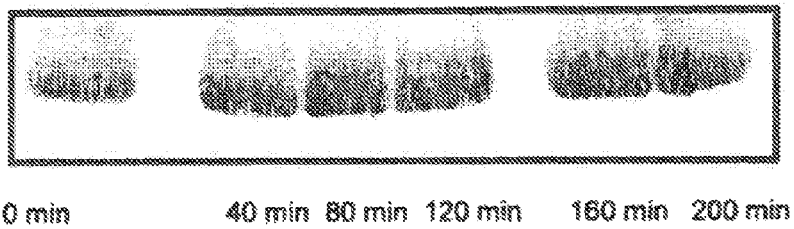

Protease susceptibility of SAK derivatives and their PEG conjugated forms: In order to check the response of SAK derivatives and their PEG linked forms against protease susceptibility, native SAK and its PEG derivatives and their unmodified forms were tested against a general protease, i.e., Trypsin. 100 μg of each SAK derivative and the native SAK was incubated with Trypsin in 100:1 and 200:1 ratio (w/w) in 10 mM Tris.Cl (pH 8.0) and 50 mM NaCl for 1 to 2 hr at 37° C. and an aliquot was taken out at different intervals of time and analyzed on SDS-PAGE. PEG conjugated derivatives of SAK displayed significant increase in resistance against trypsin attack as compared to unmodified as well as wild type SAK (FIG. 4).

Example 7

Figure 5:
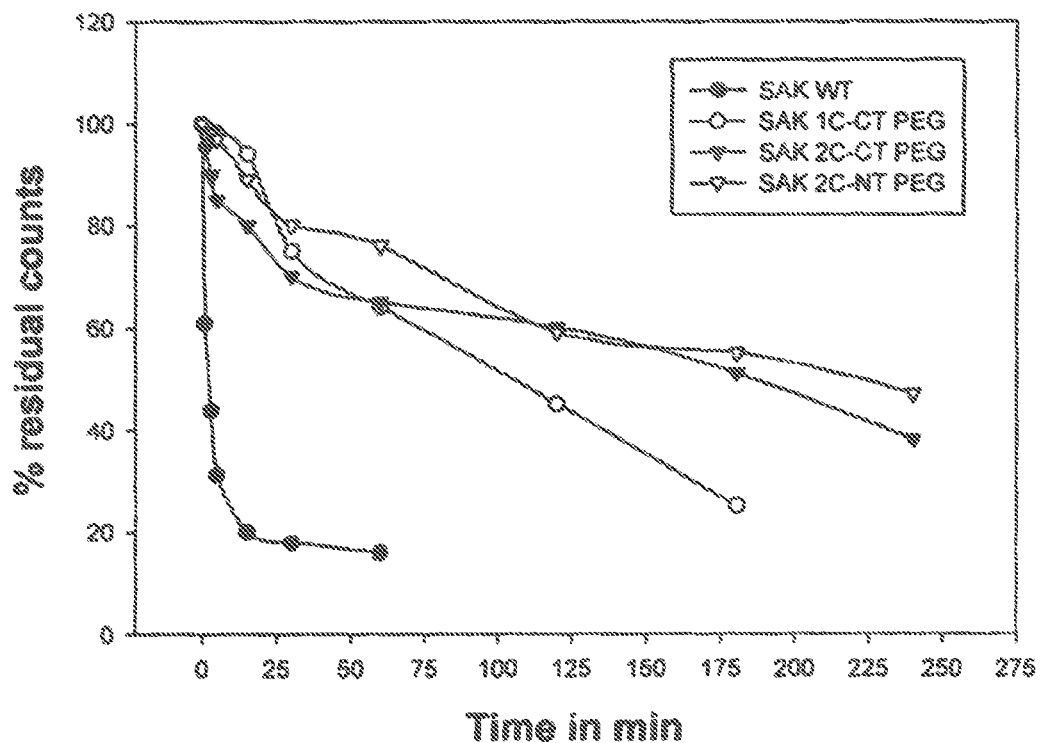
FIG. 5. Half life of wild type and PEG conjugated SAK mutants.

Testing of in vivo plasma half life of SAK derivatives and their PEG conjugated forms: Since native SAK and SAK derivatives were expressed in a bacterial host, *E. coli*, presence of some endotoxins in the purified protein can be expected. To remove endotoxins from the protein preparation, each SAK derivatives as well as wild type SAK protein was passed twice through a Polymyxin B Agarose column (Sigma Aldrich) and then used for animal studies. Endotoxin free preparation of SAK derivatives as well as wild type SAK was radiolabelled with 1125 following known procedures [Fraker, P. J., Speck, J. C. (1978) Protein and cell membrane iodination with a sparingly soluble choramide 1,3,4,6-tetrachloro-3a,6a-diphenylgylycoril. Biochem. Biophys. Res. Commun. 80; 849-857] and unincorporated free iodine was removed by dialysis against 50 mM phosphate buffer. The radiolabelled preparation of SAK derivative and wild type SAK was then used for studying their pharmacological characteristics by injecting into mice to test their in vivo stability. Mice (Swiss) were used for injecting various radiolabelled SAK derivatives. First, mice were treated with 3% iso-fluorane to anaesthesize and then vasodilation was induced in the tail to inject nearly 7-8 μg of iodinated protein via the tail vein. About 30-50 μl of blood sample was collected immediately after injection and after the different intervals of time from tail vein or from ear vein. In vivo plasma half-life of SAK derivative was determined by checking the level of residual level of radioactivity left in the plasma processed from the collected sample at different time points. Simultaneously, withdrawn samples were TCA-precipitated after adding equal volume of 20% TCA into each sample and incubating on ice for 20 min. The samples were then centrifuged at 5000 rpm for 10 min and supernatant was removed to separate free radioactivity and precipitate was analyzed for the radioactivity associated with the plasma protein by checking radioactive counts left in the precipitate (FIG. 5). The results were further confirmed by autoradiography after running the samples on SDS-PAGE. Two independent sets of experiments were conducted to conclude the results.

Results show that different PEG conjugated SAK derivatives have different degrees of in vivo plasma half-life as shown in Table 3. Integration of two cysteines in SAK results in 5-8 fold increase in plasma half life than SAK derivatives carrying only one cysteine. Also, the presence of cysteine in the extended amino and carboxy ends of SAK have different effects on in vivo stability of SAK. Retention of SAK derivatives in animal model was also tested by taking blood samples at different time points and checking the retention of protein by autoradiography which indicated that after 5 minutes of injection, wild type SAK gets cleared from the blood sample, whereas, PEG conjugated SAK derivatives are retained in the blood for a longer time. Retention time differed in case of different mutants as shown in Table. 3.

TABLE 3

In vivo plasma half life of SAK derivatives injected in mice

| SAK Derivatives | In vivo Plasma Half-Life |
| --- | --- |
| SAK | <5 min |
| SAK S3C-PEG kDa | ~20 min |
| SAK 1CNT PEG 20 kDa | >60 min |
| SAK 2CNT PEG 20 kDa | >3 h |
| SAK 1CCT PEG 20 kDa | >90 min |
| SAK 2CCT PEG 20 kDa | >3 h |
| SAK 1CCT PEG 5 kDa | >10 min |
| SAK 1CCT PEG 10 kDa | >20 min |
| SAK 2CCT PEG 5 kDa | >40 min |
| SAK 2CCT PEG 10 kDa | >90 min |

Example 8

Immunogenicity of PEGylated cysteine derivatives of SAK: To check the immunogenicity of various SAK cysteine derivatives, polyclonal antisera raised against SAK in rabbit was used to check the reactivity with various PEGylated SAK derivatives and WT SAK by ELISA plate method. The microtitre plate was incubated at 4° C. overnight with 100 μl/well of SAK and PEGylated cysteine mutants containing 1 μg of protein in coating buffer i.e. 0.2 M bicarbonate buffer pH 9.2. The coated plates were washed with 200 μl PBS-T (PBS, pH 7.5, containing 0.05% v/v Tween 20) three times for 10 min each. The unoccupied sites were blocked with 5% skim milk in PBS-T and kept for 2 hrs at 37° C. The plate was washed with 200 μl PBS-T three times. 100 μl of diluted (1:40000 in PBS) primary antibody against SAK was added to each well and incubated at 37° C. for 4 hrs. After three washings, 100 μl of HRP conjugated antibody was added in 1:5000 dilutions and kept for 1 hr at 37° C. The plate was washed three times with PBS. 1000 of TMB substrate was added to each well and incubated for 20-30 min at 37° C. Finally 50 μl of H2SO4 was added to stop the reaction and the plate was read at 450 nm. The immmunoreactivity of SAK and different PEGylated derivatives was evaluated by comparing the absorbance values. The SAK cysteine derivatives showed varied degrees of immunoreactivity against polyclonal sera of SAK. The percentage reactivity of all SAK derivatives has been shown in Table 4.

TABLE 4

Immunogenicity of PEGylated cysteine derivatives of SAK

| SAK Derivatives | Percentage Immunoreactivity |
| --- | --- |
| PEG 1CCT 5 kDa | 70% |
| PEG 2CCT 5 kDa | 65-70% |
| PEG 1CCT 10 kDa | 60% |
| PEG 2CCT 10 kDa | 50% |
| PEG 1CCT 20 kDa | 35-40% |
| PEG 2CCT 20 kDa | 30-35% |

Based on the above disclosure, it is evident that the present invention offers flexibility of designing new amino acid sequences for a single and a multiple PEG conjugation which can improve the functional properties of staphylokinase without interference in its native sequence. This is because the mutations are not done in the native peptide but rather in the introduced N and C terminal extensions which therefore does not affect the inherent properties of the SAK protein.

The PEG conjugated derivatives of Staphylokinase mentioned in the present invention display the following advantages: they have increased plasma half life, increased temperature stability, low immune reactivity and increased clinical potential of SAK for the treatment of thrombolytic complications.

We claim:

1. A Staphylokinase variant comprising the amino acid sequence of SEQ ID NO: 5, wherein the C-terminal cysteine residue of SEQ ID NO: 5 is conjugated to a polyethylene glycol (PEG) molecule.

2. The Staphylokinase variant of claim 1, wherein the conjugated PEG molecule is a branched PEG molecule.

3. The Staphylokinase variant of claim 2, wherein the molecular size of the PEG molecule ranges from 5-20 Kilodaltons.

4. The Staphylokinase variant of claim 1, wherein the variant has proteolytic stability which is greater than the proteolytic stability of the polypeptide identified as SEQ ID NO:1, wherein proteolytic stability of the Staphylokinase variant and of the polypeptide identified as SEQ ID NO:1 is measured in vitro at a pH of about 8 and at a temperature of about 37° C. in the presence of trypsin.

5. The Staphylokinase variant of claim 1, wherein the variant has in vivo immunogenicity which is less that the in vivo immunogenicity of the polypeptide identified as SEQ ID NO:1.

6. The Staphylokinase variant of claim 1, wherein the variant has an in vivo half life which is greater than the in vivo half life of the polypeptide identified as SEQ ID NO:1.

7. The Staphylokinase variant of claim 1, wherein the variant has temperature stability which is greater than the temperature stability of the polypeptide identified as SEQ ID NO:1, wherein the temperature stability is determined at a temperature ranging from about 20° C. to about 80° C.

8. The Staphylokinase variant of claim 1, wherein the conjugated PEG molecule is a linear PEG molecule.

* * * * *

SEQUENCE LISTING

```
<160> NUMBER OF SEQ ID NOS: 7

<210> SEQ ID NO 1
<211> LENGTH: 136
<212> TYPE: PRT
<213> ORGANISM: Staphylococcus aureus

<400> SEQUENCE: 1

Ser Ser Ser Phe Asp Lys Gly Lys Tyr Lys Lys Gly Asp Asp Ala Ser
1               5                   10                  15

Tyr Phe Glu Pro Thr Gly Pro Tyr Leu Met Val Asn Val Thr Gly Val
            20                  25                  30

Asp Gly Lys Gly Asn Glu Leu Leu Ser Pro His Tyr Val Glu Phe Pro
        35                  40                  45

Ile Lys Pro Gly Thr Thr Leu Thr Lys Glu Lys Ile Glu Tyr Tyr Val
    50                  55                  60

Glu Trp Ala Leu Asp Ala Thr Ala Tyr Lys Glu Phe Arg Val Val Glu
65                  70                  75                  80

Leu Asp Pro Ser Ala Lys Ile Glu Val Thr Tyr Tyr Asp Lys Asn Lys
                85                  90                  95

Lys Lys Glu Glu Thr Lys Ser Phe Pro Ile Thr Glu Lys Gly Phe Val
            100                 105                 110

Val Pro Asp Leu Ser Glu His Ile Lys Asn Pro Gly Phe Asn Leu Ile
        115                 120                 125
```

Thr Lys Val Val Ile Glu Lys Lys
    130             135

<210> SEQ ID NO 2
<211> LENGTH: 411
<212> TYPE: DNA
<213> ORGANISM: Staphylococcus aureus

<400> SEQUENCE: 2
tcaagttcat tcgacaaagg aaaatataaa aagggcgatg acgcgagtta ttttgaacca    60
acaggcccgt atttgatggt aaatgtgact ggagttgatg gtaaaggaaa tgaattgcta   120 tccctcatt atgtcgagtt tcctattaaa cctgggacta cacttacaaa agaaaaaatt   180
gaatactatg tcgaatgggc attagatgcg acagcatata aagagtttag agtagttgaa   240
ttagatccaa gcgcaaagat cgaagtcact tattatgata agaataagaa aaagaagaa   300 acgaagtctt tccctataac agaaaaaggt tttgttgtcc cagatttatc agagcatatt   360
aaaaaccctg gattcaactt aattacaaag gttgttatag aaaagaaata a            411

<210> SEQ ID NO 3
<211> LENGTH: 138
<212> TYPE: PRT
<213> ORGANISM: Staphylococcus aureus

<400> SEQUENCE: 3

Met Cys Ser Ser Ser Phe Asp Lys Gly Lys Tyr Lys Lys Gly Asp Asp
1               5                   10                  15

Ala Ser Tyr Phe Glu Pro Thr Gly Pro Tyr Leu Met Val Asn Val Thr
            20                  25                  30

Gly Val Asp Gly Lys Gly Asn Glu Leu Leu Ser Pro His Tyr Val Glu
        35                  40                  45

Phe Pro Ile Lys Pro Gly Thr Thr Leu Thr Lys Glu Lys Ile Glu Tyr
    50                  55                  60

Tyr Val Glu Trp Ala Leu Asp Ala Thr Ala Tyr Lys Glu Phe Arg Val
65                  70                  75                  80

Val Glu Leu Asp Pro Ser Ala Lys Ile Glu Val Thr Tyr Tyr Asp Lys
                85                  90                  95

Asn Lys Lys Lys Glu Glu Thr Lys Ser Phe Pro Ile Thr Glu Lys Gly
            100                 105                 110

Phe Val Val Pro Asp Leu Ser Glu His Ile Lys Asn Pro Gly Phe Asn
        115                 120                 125

Leu Ile Thr Lys Val Val Ile Glu Lys Lys
    130                 135

<210> SEQ ID NO 4
<211> LENGTH: 139
<212> TYPE: PRT
<213> ORGANISM: Staphylococcus aureus

<400> SEQUENCE: 4

Met Cys Cys Ser Ser Ser Phe Asp Lys Gly Lys Tyr Lys Lys Gly Asp
1               5                   10                  15

Asp Ala Ser Tyr Phe Glu Pro Thr Gly Pro Tyr Leu Met Val Asn Val
            20                  25                  30

Thr Gly Val Asp Gly Lys Gly Asn Glu Leu Leu Ser Pro His Tyr Val
        35                  40                  45

Glu Phe Pro Ile Lys Pro Gly Thr Thr Leu Thr Lys Glu Lys Ile Glu

```
                50                  55                  60
Tyr Tyr Val Glu Trp Ala Leu Asp Ala Thr Ala Tyr Lys Glu Phe Arg
 65                  70                  75                  80

Val Val Glu Leu Asp Pro Ser Ala Lys Ile Glu Val Thr Tyr Tyr Asp
                 85                  90                  95

Lys Asn Lys Lys Lys Glu Glu Thr Lys Ser Phe Pro Ile Thr Glu Lys
                100                 105                 110

Gly Phe Val Val Pro Asp Leu Ser Glu His Ile Lys Asn Pro Gly Phe
                115                 120                 125

Asn Leu Ile Thr Lys Val Val Ile Glu Lys Lys
                130                 135

<210> SEQ ID NO 5
<211> LENGTH: 138
<212> TYPE: PRT
<213> ORGANISM: Staphylococcus aureus

<400> SEQUENCE: 5

Ser Ser Ser Phe Asp Lys Gly Lys Tyr Lys Lys Gly Asp Asp Ala Ser
  1               5                  10                  15

Tyr Phe Glu Pro Thr Gly Pro Tyr Leu Met Val Asn Val Thr Gly Val
                 20                  25                  30

Asp Gly Lys Gly Asn Glu Leu Leu Ser Pro His Tyr Val Glu Phe Pro
                 35                  40                  45

Ile Lys Pro Gly Thr Thr Leu Thr Lys Glu Lys Ile Glu Tyr Tyr Val
 50                  55                  60

Glu Trp Ala Leu Asp Ala Thr Ala Tyr Lys Glu Phe Arg Val Val Glu
 65                  70                  75                  80

Leu Asp Pro Ser Ala Lys Ile Glu Val Thr Tyr Tyr Asp Lys Asn Lys
                 85                  90                  95

Lys Lys Glu Glu Thr Lys Ser Phe Pro Ile Thr Glu Lys Gly Phe Val
                100                 105                 110

Val Pro Asp Leu Ser Glu His Ile Lys Asn Pro Gly Phe Asn Leu Ile
                115                 120                 125

Thr Lys Val Val Ile Glu Lys Lys Ala Cys
                130                 135

<210> SEQ ID NO 6
<211> LENGTH: 138
<212> TYPE: PRT
<213> ORGANISM: Staphylococcus aureus

<400> SEQUENCE: 6

Ser Ser Ser Phe Asp Lys Gly Lys Tyr Lys Lys Gly Asp Asp Ala Ser
  1               5                  10                  15

Tyr Phe Glu Pro Thr Gly Pro Tyr Leu Met Val Asn Val Thr Gly Val
                 20                  25                  30

Asp Gly Lys Gly Asn Glu Leu Leu Ser Pro His Tyr Val Glu Phe Pro
                 35                  40                  45

Ile Lys Pro Gly Thr Thr Leu Thr Lys Glu Lys Ile Glu Tyr Tyr Val
 50                  55                  60

Glu Trp Ala Leu Asp Ala Thr Ala Tyr Lys Glu Phe Arg Val Val Glu
 65                  70                  75                  80

Leu Asp Pro Ser Ala Lys Ile Glu Val Thr Tyr Tyr Asp Lys Asn Lys
                 85                  90                  95

Lys Lys Glu Glu Thr Lys Ser Phe Pro Ile Thr Glu Lys Gly Phe Val
```

```
                    100                 105                  110
Val Pro Asp Leu Ser Glu His Ile Lys Asn Pro Gly Phe Asn Leu Ile
        115                 120                 125

Thr Lys Val Val Ile Glu Lys Lys Cys Cys
    130                 135

<210> SEQ ID NO 7
<211> LENGTH: 136
<212> TYPE: PRT
<213> ORGANISM: Staphylococcus aureus

<400> SEQUENCE: 7

Ser Ser Cys Phe Asp Lys Gly Lys Tyr Lys Lys Gly Asp Asp Ala Ser
1               5                   10                  15

Tyr Phe Glu Pro Thr Gly Pro Tyr Leu Met Val Asn Val Thr Gly Val
            20                  25                  30

Asp Gly Lys Gly Asn Glu Leu Leu Ser Pro His Tyr Val Glu Phe Pro
        35                  40                  45

Ile Lys Pro Gly Thr Thr Leu Thr Lys Glu Lys Ile Glu Tyr Tyr Val
    50                  55                  60

Glu Trp Ala Leu Asp Ala Thr Ala Tyr Lys Glu Phe Arg Val Val Glu
65                  70                  75                  80

Leu Asp Pro Ser Ala Lys Ile Glu Val Thr Tyr Tyr Asp Lys Asn Lys
                85                  90                  95

Lys Lys Glu Glu Thr Lys Ser Phe Pro Ile Thr Glu Lys Gly Phe Val
            100                 105                 110

Val Pro Asp Leu Ser Glu His Ile Lys Asn Pro Gly Phe Asn Leu Ile
        115                 120                 125

Thr Lys Val Val Ile Glu Lys Lys
    130                 135
```